United States Patent
Nishimura et al.

(10) Patent No.: US 10,577,446 B2
(45) Date of Patent: Mar. 3, 2020

(54) RESIN PRECURSOR COMPOSITION FOR OPTICAL MATERIALS, OPTICAL ELEMENT OBTAINED FROM THE COMPOSITION, AND DIFFRACTIVE OPTICAL ELEMENT CONFIGURED USING THE OPTICAL ELEMENT

(71) Applicant: NIKON CORPORATION, Tokyo (JP)

(72) Inventors: Shiho Nishimura, Sagamihara (JP); Yosuke Inokuchi, Tokyo (JP)

(73) Assignee: Nikon Corporation, Tokyo (JP)

(*) Notice: Subject to any disclaimer, the term of this patent is extended or adjusted under 35 U.S.C. 154(b) by 0 days.

(21) Appl. No.: 16/207,617

(22) Filed: Dec. 3, 2018

(65) Prior Publication Data

US 2019/0112405 A1    Apr. 18, 2019

Related U.S. Application Data

(63) Continuation of application No. 15/441,698, filed on Feb. 24, 2017, now abandoned, which is a continuation of application No. PCT/JP2015/004305, filed on Aug. 26, 2015.

(30) Foreign Application Priority Data

Aug. 26, 2014 (JP) ................. 2014-171667

(51) Int. Cl.
| | |
|---|---|
| *C07C 69/003* | (2006.01) |
| *G02B 5/18* | (2006.01) |
| *C08F 222/18* | (2006.01) |
| *G02B 1/04* | (2006.01) |
| *C07C 69/54* | (2006.01) |
| *C08G 75/045* | (2016.01) |
| *C08F 122/10* | (2006.01) |

(52) U.S. Cl.
CPC .......... *C08F 222/18* (2013.01); *C07C 69/003* (2013.01); *C07C 69/54* (2013.01); *C08F 122/105* (2013.01); *C08G 75/045* (2013.01); *G02B 1/04* (2013.01); *G02B 5/1852* (2013.01); *G02B 5/1866* (2013.01)

(58) Field of Classification Search
CPC combination set(s) only.
See application file for complete search history.

(56) References Cited

U.S. PATENT DOCUMENTS

| | | |
|---|---|---|
| 2003/0161044 A1 | 8/2003 | Tokoyoda |
| 2006/0268414 A1 | 11/2006 | Tokoyoda |
| 2008/0094712 A1 | 4/2008 | Miyakawa |
| 2008/0107903 A1 | 5/2008 | Miyakawa et al. |
| 2009/0273841 A1 | 11/2009 | Tokoyoda |

FOREIGN PATENT DOCUMENTS

| | | |
|---|---|---|
| JP | H1-238553 A | 9/1989 |
| JP | 2003-262713 A | 9/2003 |
| JP | 2005-029608 A | 2/2005 |
| JP | 2005-035968 A | 2/2005 |
| JP | 2006-002129 A | 1/2006 |
| JP | 4760714 B2 | 8/2011 |
| JP | 2014-171666 A | 9/2014 |
| JP | 2016-044285 A | 4/2016 |
| WO | 2006/068138 A1 | 6/2006 |

OTHER PUBLICATIONS

Suzuki, "Enlarged and Revised Edition, Introduction of Diffractive Optical Element", 163 (Optronics Co. Ltd., 1997), pp. 166-168, 4, "Development of closely contacted multi-layer PF (Phase Fresnel) Lens", 4.1 Basic Configuration of Grating/Measure against Flare.
International Search Report dated Oct. 13, 2015, for corresponding International application No. PCT/JP2015/004305.
Translation of Written Opinion of the International Searching Authority dated Oct. 13, 2015, for corresponding International Application No. PCT/JP2015/004305.
Office Action dated Feb. 6, 2018, issued in counterpart Japanese Patent Application No. 2016-544966.
Extended European Search Report dated Feb. 14, 2018, issued in counterpart European Patent Application No. 15836632.8.
Office Action dated Sep. 18, 2018, issued in corresponding Japanese Patent Application No. 2016-544966.
Office Action dated Oct. 24, 2018, issued in corresponding European Patent Application No. 15836632.8.

*Primary Examiner* — Ana Z Muresan
(74) *Attorney, Agent, or Firm* — Morgan, Lewis & Bockius LLP (57) ABSTRACT

Low refractive index and high dispersion material which can produce a bonded-multilayer DOE having an excellent optical performance is obtained, and the optical member using this is obtained. The resin precursor for optical materials obtained through the addition reaction of the composite containing a di (meth) acrylate shown in the following Chemical Expression 1.

Chemical Expression 1:

(Chemi. 1)

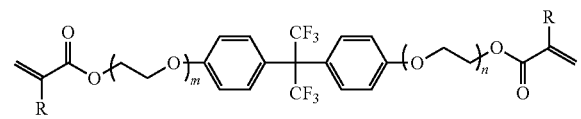

where, R=H or $CH_3$, and m+n=1 to 10.

6 Claims, 7 Drawing Sheets

RESIN PRECURSOR COMPOSITION FOR OPTICAL MATERIALS, OPTICAL ELEMENT OBTAINED FROM THE COMPOSITION, AND DIFFRACTIVE OPTICAL ELEMENT CONFIGURED USING THE OPTICAL ELEMENT

RELATED APPLICATIONS

This application is a continuation application od U.S. application Ser. No. 15/441,698 filed on Feb. 24, 2017, which is a continuation of PCT International Application No. PCT/JP2015/004305, filed on Aug. 26, 2015, which is hereby incorporated by reference. This application also claims the benefit of Japanese Patent Application No. 2014-171667, filed in Japan on Aug. 26, 2014, which is hereby incorporated by reference.

TECHNICAL FIELD

The present invention relates to a resin precursor composite having a property of low refractive index and high dispersion and suitable for using as a multilayer diffractive optical element, and an optical member using this resin precursor composite, additionally, an optical element (specifically, diffractive optical element) obtained with a combination of this optical material and a resin with a property such as high refractive index and low dispersion.

TECHNICAL BACKGROUND

Efforts to incorporate a diffractive optical element to an optical system have been attempted for many years, especially, a diffractive optical element, which is processed a grating height to be an equivalent to one wavelength, that is, a phase difference $2\pi$, can concentrate lights to the 1st order diffracted light, therefore, usage aiming at achieving a small size and weight-saving and a correction of chromatic aberration of an optical system has been considered.

However, in case of a single layer diffractive optical element whose grating surface is exposed to air, the 1st order diffraction efficiency can become 100% at a reference wavelength, although other-order diffracted lights increase as the wavelength shifts away from the reference wavelength, and this becomes diffraction flare lights, there was still a problem of degrading optical performance. In order to solve this problem, a bonded-multilayer diffractive optical element having a configuration where two gratings, composed of characteristic two kinds of resins, are bonded, was devised (for example, Documents 1 and 2). That is, $$(n2-n1) \times h = \lambda \quad (1)$$

In the expression (1), n1 and n2 respectively denote refractive indexes (n2>n1) of the resins, h denotes a grating height of the diffractive optical element, and $\lambda$ denotes a wavelength.

If equality of the expression (1) always holds within a usage wavelength range, the diffraction efficiency of the 1st order light becomes 100% within a whole range of the usage wavelength range, thereby this enables to prevent generation of diffraction flares due to the diffracted lights.

PRIOR ART LIST

Patent Document

[Patent Document 1] Japanese Laid-Open Patent Publication No. 2003-262713(A)

Non Patent Document

[Non Patent Document 1] Kenzaburo Suzuki: "Enlarged and Revised Edition, Introduction of Diffractive Optical Element," 163 (Optronics Co. Ltd., 1997)

SUMMARY OF THE INVENTION

Problems to be Solved by the Invention

According to the expression (1), it is found that the refractive index difference (n2-n1) of the resins has a proportional relationship with the wavelength. In order that the refractive index difference of two resins becomes larger as the wavelength becomes longer, it is required that the first resin (refractive index n1) is composed of low refractive index and high dispersion resin and the second resin (refractive index n2) is composed of high refractive index and low dispersion resin. In other words, a combination of the resins, in which the difference of the dispersion values (Abbe numbers or mean dispersion (nF-nC)) of the two resins becomes large, is required. Since the grating height h can be made lower as the refractive index difference (n2-n1) of the two resins is larger, a process of the grating becomes easier.

However, there is a tendency for general resins that a dispersion value becomes larger as a refractive index becomes larger, and a dispersion value becomes smaller as a refractive index becomes smaller. Therefore, it is not easy to combine a resin having high refractive index and low dispersion and a resin having low refractive index and high dispersion, and also to make the refractive index difference become large, and development of a new resin has been required in order to produce the bonded-multilayer diffractive optical element which has outstanding optical performance.

Additionally, the bonded-multilayer diffractive optical element has a condition that has to be satisfied depending on its usage. For example, in order to apply the bonded-multilayer diffractive optical element to a optical system which performs observation or a measurement using fluorescence such as a biological system microscope, in addition to the condition of the refractive index dispersion above, it is necessary to have both of an required transmittance within an excitation wavelength (usually including ultraviolet) of the fluorescence and suppression of causing autofluorescence from the bonded-multilayer diffractive optical element itself within very small amount. In order to apply the bonded-multilayer diffractive optical element to the interchangeable lens for cameras, it might be important to suppress a change of the diffraction flare generated by diffracted lights below tolerance even if the orientation of light incident on the diffractive optical element changes.

In view of the situation above, the present invention aims at obtaining a resin having lower refractive index and higher dispersion in comparison with the conventional resins, and an optical member using this, further obtaining a bonded-multilayer diffractive optical element by combining this resin with high refractive index and low dispersion resin in order to satisfy a condition depending on its usage.

Means to Solve the Problems

A resin precursor composite for optical material for solving the above problem, comprises a composite containing a bisphenol AF ethyleneoxide modified di (meth) acrylate shown in the following Chemical Expression 1.

Note that a resin precursor is a composite which turns into a cured resin by curing, and may contain any of monomers, oligomers, prepolymers, and polymers.

Chemical Expression 1:

(Chemi. 1)

where, R=H or $CH_3$, and m+n=1 to 10.

A resin precursor composite for optical material for solving the above problems, preferably comprises a bisphenol AF ethyleneoxide modified di (meth) acrylate shown in the above-mentioned Chemical Expression 1 being m=1, and n=1.

The resin precursor composite according to the present invention may comprise the composite shown in the Chemical Expression 1 above and a polymerization initiator. The additive amount of the polymerization initiator in this situation is preferably 0.05 to 3 wt % against the optical material. This additive amount is more preferably 0.07 to 0.7 wt % against the optical material.

A optical member for solving the above problems is obtained by curing the any one of above-mentioned resin precursor composite.

A diffractive optical element for solving the above problems is composed of a diffraction grating in which a diffraction grating is formed at a boundary surface by laminating the above mentioned optical member and an optical member having higher refractive index and lower dispersion than the above mentioned optical member.

A diffractive optical element for solving the above problems, in which the optical member having higher refractive index and lower dispersion is obtained by curing an addition reactant of a composite containing a thiol shown in Chemical Expression 2 and a di (meth) acrylate.

Chemical Expression 2:

(Chemi. 2)

where, m+n=1-6.

In the diffractive optical element for solving the above problems, the di (meth) acrylate is shown in the following Chemical Expression 3.

Chemical Expression 3:

(Chemi. 3)

where, R=H or $CH_3$, m+n=1 to 10.

Advantageous Effects of the Invention

The resin precursor composite according to the present invention mentioned above is a material having low refractive index and high dispersion, and is appropriate for usage of a bonded-multilayer diffractive optical member, the optical element according to the present invention is composed of a combination with the resin having low refractive index and high dispersion and the resin having high refractive index and low dispersion.

DESCRIPTION OF THE EMBODIMENTS

Firstly, a resin precursor composite having low refractive index and high dispersion is explained as a preferable example of the present application. This resin precursor composite contains bisphenol AF ethyleneoxide modified di (meth) acrylate shown in the following Chemical Expression 1. This material has comparatively low refractive index and high dispersion, and has a low fluorescent bisphenol AF framework. Since a benzene ring showing a high dispersion property has a conjugated double bond, autofluorescence becomes large depending on its disposition. In the present invention, the autofluorescence of a resin obtained by curing this resin precursor composite is also suppressed by disposing a benzene ring via one or more carbons as shown in the following Chemical Expression 1.

Chemical Expression 1:

(Chemi. 4)

where, R=H or $CH_3$, and m+n=1 to 10.

The bisphenol AF ethyleneoxide modified di (meth) acrylate of Chemical Expression 1 has lower refractive index and higher dispersion property as values of m and n are smaller, it is preferable that the values of m and n are small. However, when n+m=0 or 1, it is solid or has a high viscosity at an ordinary temperature, and it is difficult to handle it. Accordingly, in Examples 1 and 3, m=1, n=1 and R=$CH_3$ which are considered especially preferable, and the 2,2-bis (4-(2-(meth)cryloyloxy) ethoxy) phenyl-1,1,1,3,3,3-hexafluoropropane commonly-named BMHF, is used. In Example 2, R=H, m=1 and n=1, and the 2,2-bis(4-(2-acryloyloxy)ethoxy) phenyl-1,1,1,3,3,3-hexafluoropropane commonly-named "BAHF," is used.

The resin precursor shown in Chemical Expression 1 above is liquid at an ordinary temperature, and cannot constitute an optical member in this state. Thus, light or thermal polymerization initiator is added to this resin precursor composite, and this will be cured by irradiating ultraviolet or applying heat. Note that an optical member used in a lens, diffractive optical element, etc. can be produced by molding or fabricating this to the desired shape during the curing process of the ultraviolet irradiation or the heat application, or after the curing.

Firstly, as Examples 1 and 2, a precursor composite was prepared by adding 0.1 wt % of IRGACURE184 (manufactured by BASF Japan Co., Ltd.) which is a photo polymerization initiator to the two kinds above of the bisphenol AF ethyleneoxide modified di (meth) acrylate.

Also, as Example 3, the precursor composite was prepared by adding 0.5 wt % of IRGACURE184 to the 2,2-bis (4-(2-(meth)cryloyloxy) ethoxy) phenyl-1,1, 13,3,3-hexafluoropropane (BMHF).

EXAMPLE 1

BMHF, IRGACURE184 0.1 wt %

EXAMPLE 2

BAHF, IRGACURE184 0.1 wt %

EXAMPLE 3

BMHF, IRGACURE184 0.5 wt %

Furthermore, a conventional optical material (named as "Conventional Material a") was prepared as a comparative example. Conventional Material a is a material according to Japanese Patent No. 4760714 owned by the present applicant, and is an optical material which was cured by the ultraviolet irradiation to the resin precursor composite b described as Example 1 in the specification of the patent publication. This resin precursor composite a is adjusted by adding 0.5 wt % of the photo polymerization initiator IRGACURE184 to 53 wt % of the 2,2,3,3,4,4,5,5,-octafluorohexane-1, 6-diacrylate which is bifunctional fluorine acrylate, 42 wt % of the 9,9-bis[4-(2-acryloyloxy ethoxy) phenyl] fluorene which is bifunctional acrylate having a fluorene framework, and 5 wt % of the 2-phenoxyethylene glycolacrylate which is monofunctional acrylate.

Comparative example: 2,2,3,3,4,4,5,5,-octafluorohexane-1, 6-diacrylate 53 wt %, 9,9-bis[4-(2-acryloyloxy ethoxy) phenyl] fluorene 42 wt %, 2-phenoxyethylene glycolacrylate 5 wt %, and photo polymerization initiator IRGACURE184 0.5 wt %

These resin precursor composites were respectively put in between two quartz substrates which were processed by silane coupling, and the ultraviolet was irradiated in this state so that the cured resins were produced. In this situation, a distance between the two quartz substrates was adjusted so that these thicknesses of the resin precursor composites become 100 μm. Also, the ultraviolet irradiation was performed using the ultraviolet irradiation equipment (manufactured by U-VIX Corporation) having an LED which generates 365 nm ultraviolet. In this situation, through the ground glass, the irradiation for 60 seconds was performed at 25 mW/cm$^2$ as a provisional curing, and subsequently the irradiation for 250 seconds was performed at 40 mW/cm$^2$ as a real curing. A light source may include 365 nm, a metal halide lamp, a high-pressure mercury lamp and LED, etc. are available. Since an LED was preferable among these in a case that the autofluorescence especially needs to be suppressed, LED was used in this example.

The resin having 100 μm thickness, produced in this way, was irradiated by the ultraviolet for long duration using the ultraviolet irradiation equipment (manufactured by U-VIX Corporation) having an LED which generates 365 nm ultraviolet, then the light resistance has been tested. The illumination intensity of the ultraviolet in this situation was 350 mW/cm$^2$, the irradiation was carried out for 216 minutes, and the fluorescence measurement and the transmittance measurement were performed after this irradiation. Note that the transmittance was measured using U-3900H manufactured by Hitachi High-Technologies Corporation. The fluorescence intensity was measured by using F-7000 manufactured by Hitachi High-Technologies Corporation.

The refractive indexes and the dispersion values of the resin fabricated by these Examples 1 to 3 and the comparative example are shown in Table 1.

TABLE 1

| Resin | nd | nF-nC |
| --- | --- | --- |
| Example 1 | 1.526 | 0.0143 |
| Example 2 | 1.529 | 0.0151 |
| Example 3 | 1.527 | 0.0144 |
| Comparative Example | 1.528 | 0.0150 |

According to Table 1, it is found that BMHF and BAHF, which are the bisphenol AF ethyleneoxide modified di (meth) acrylate resin, have a property that the refractive index was lower and the dispersion value was higher. Additionally, it is found that Conventional Material a as the comparative example, also has the property that the refractive index was higher and the dispersion value was lower.

Figure 1:
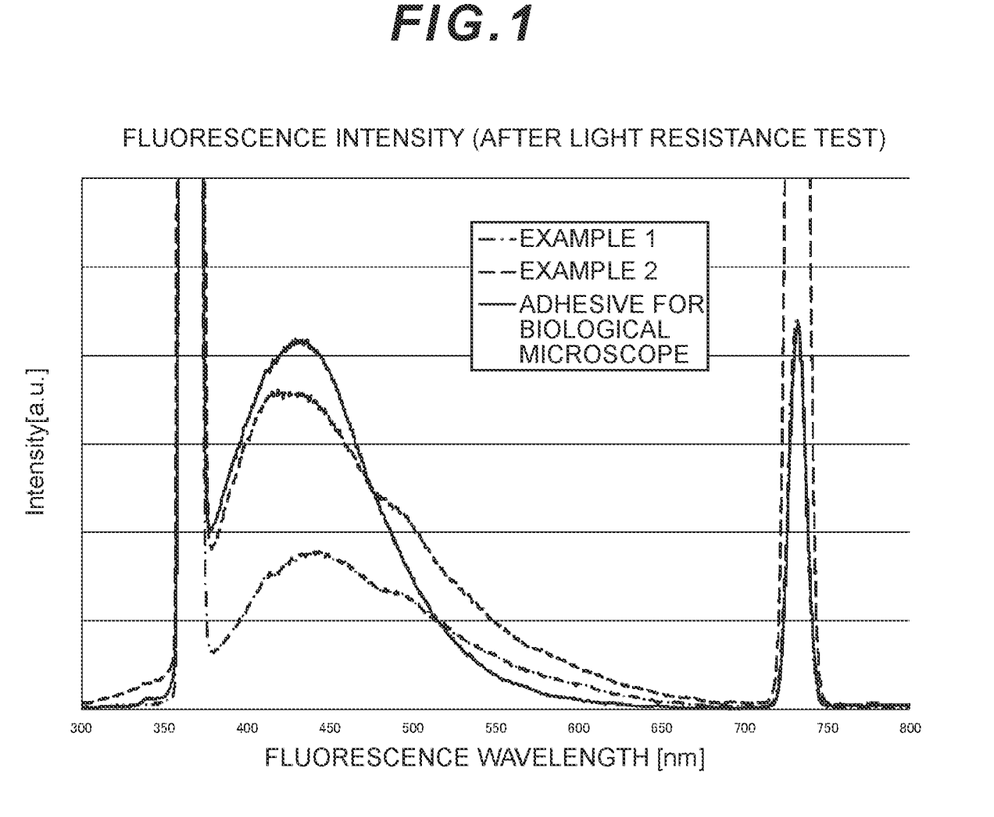
FIG. 1 illustrates a graph showing a fluorescence measurement result after a light resistance test regarding a resin having low refractive index and high dispersion of the present example above.
Figure 2:
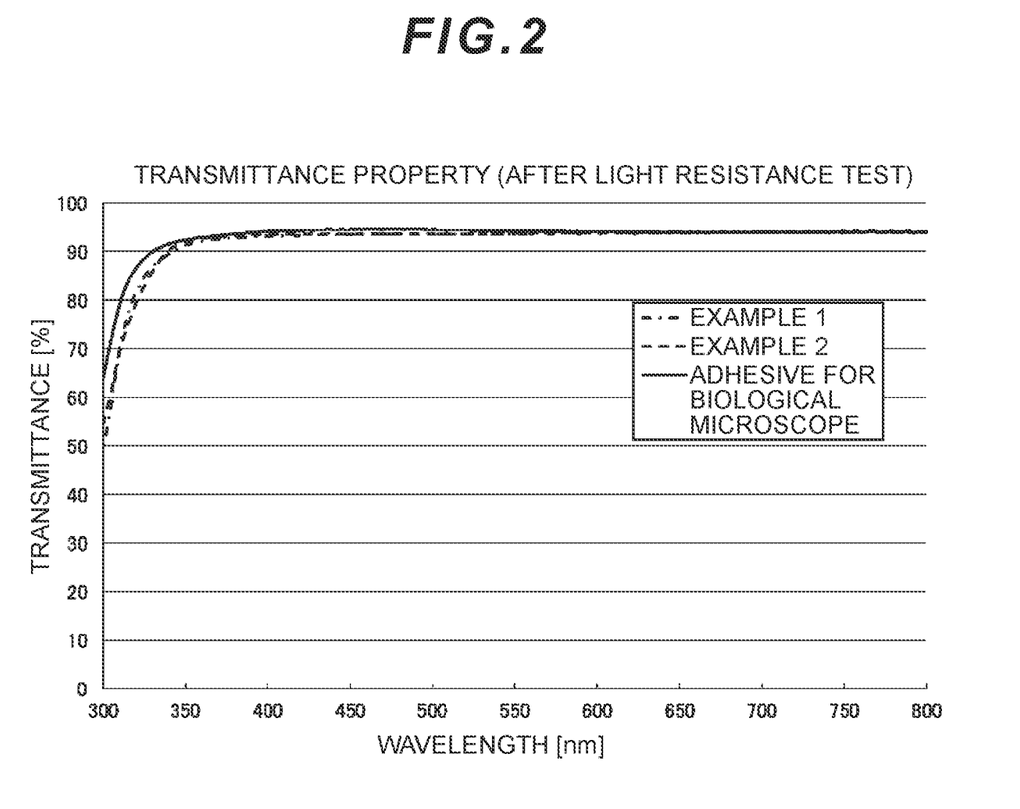
FIG. 2 illustrates a graph which shows a light transmittance measurement result after the light resistance test regarding the resin having low refractive index and high dispersion according to the present example above.

Regarding to the resins of these Examples 1 to 3 and Comparative Example, the light resistance test using the ultraviolet irradiation for long duration was performed, and the fluorescence and the transmittance were measured. The results are shown in FIG. 1 and FIG. 2. Note that this light resistance test was performed using the ultraviolet irradiation equipment (manufactured by U-VIX Corporation) having an LED which generates 365 nm ultraviolet. The illumination intensity of the ultraviolet in this situation was 350 mW/cm$^2$, the irradiation was carried out for 216 minutes, and the fluorescence measurement and the transmittance measurement were performed after this irradiation. Note that the transmittance was measured by U-3900H manufactured by Hitachi High-Technologies Corporation. The fluorescence intensity was measured by F-7000 manufactured by Hitachi High-Technologies Corporation.

FIG. 1 shows fluorescence spectra after the ultraviolet irradiation of the resins of Example 1 and Example 2, and a fluorescence spectra after the ultraviolet irradiation of the adhesive used for an objective lens of a microscope for comparison. In this figure, the horizontal axis indicates light wavelength, while the vertical axis indicates fluorescence intensity in arbitrary unit [arb.unit]. Based on the figure, it is found that the fluorescence intensity of the resin of the present invention was suppressed very small after the ultraviolet irradiation.

FIG. 2 shows the transmittance properties of Examples 1 and 2, and a transmittance property of the adhesive used to the objective lens for the microscope for comparison. As shown in FIG. 2, the resins of Examples 1 and 2 have high ultraviolet transmittance (90% or higher at 365 nm), and have high transmission performance over from the ultraviolet region to the visible region, then it is found that they are enough for usage of the fluorescence microscope objective lens for a biological system.

Furthermore, yellowing was not observed after the light resistance test above, then it is found that the resins of Examples 1 and 2 also have light resistance in this regard.

Figure 3:
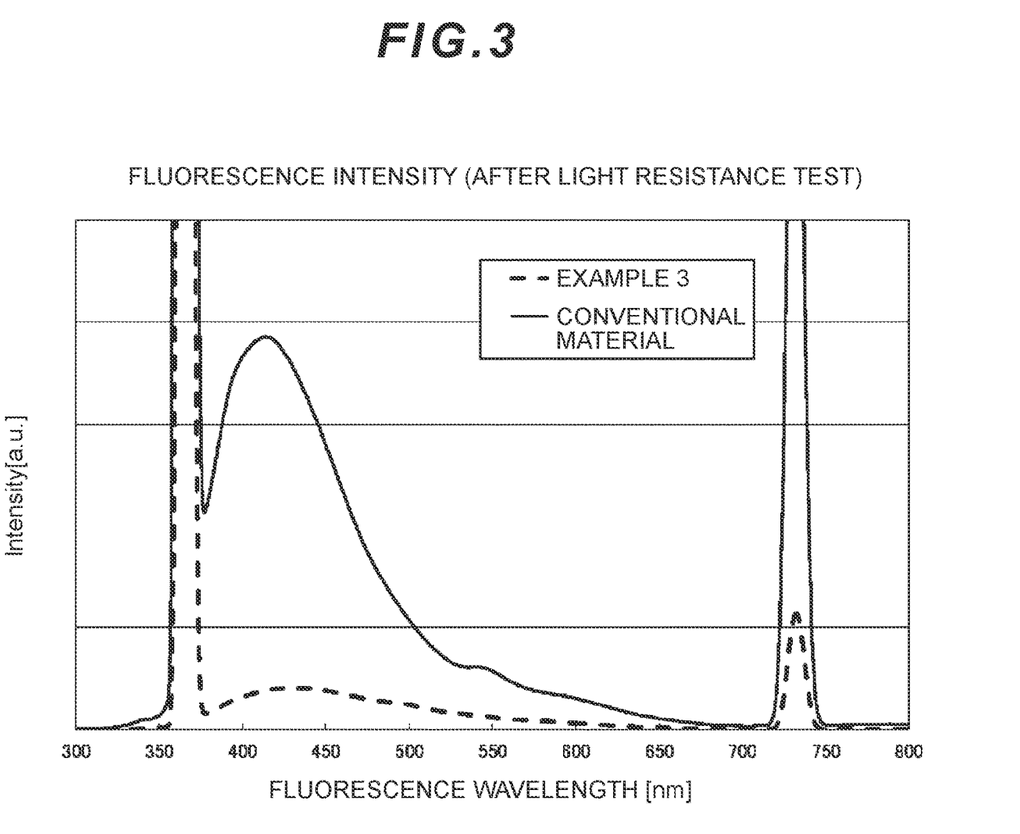
FIG. 3 illustrates a graph showing a fluorescence measurement result after the light resistance test relating to the resin having low refractive index and high dispersion according to the present example above.

Next, FIG. 3 shows a fluorescence spectra after the ultraviolet irradiation for each of the resins of Example 3 and the comparative example. In this figure, the horizontal axis indicates light wavelength, while the vertical axis indicates fluorescence intensity in arbitrary unit [arb.unit]. Based on the figure, it is found that the fluorescence intensity of the resin of the present invention was suppressed very small after the ultraviolet irradiation as compared with the conventional material.

Figure 4:
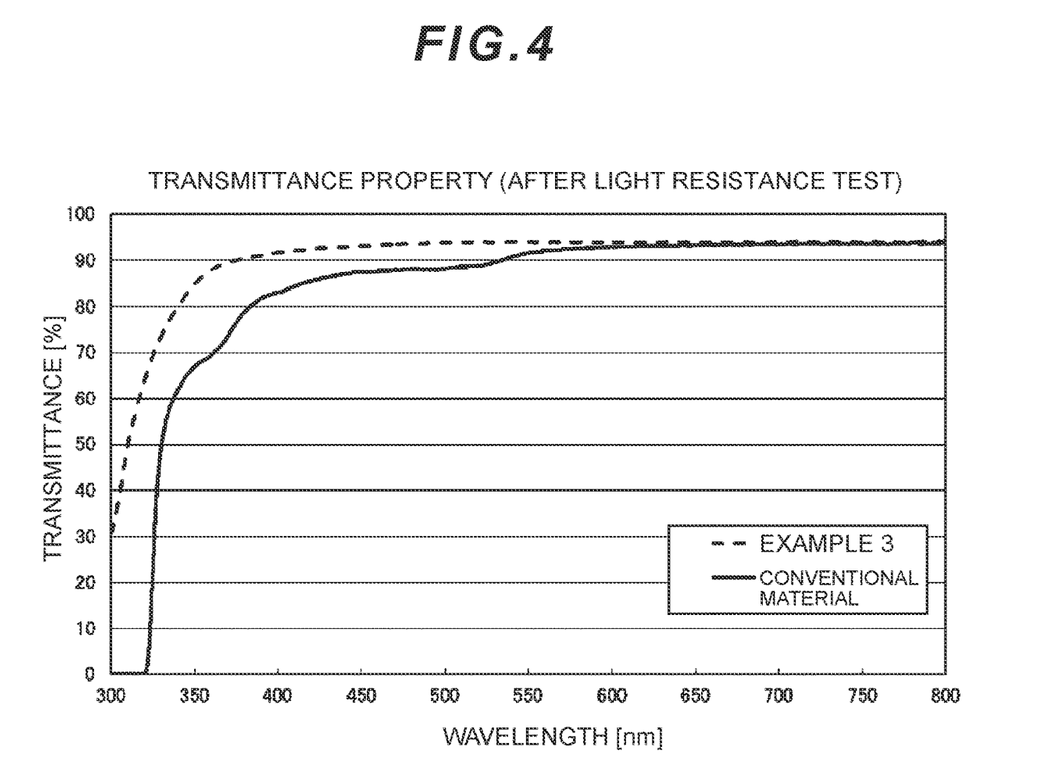
FIG. 4 illustrates a graph showing light transmittance measurement result after the light resistance test relating to the resin having low refractive index and high dispersion according to the present embodiment above.

FIG. 4 shows transmittance spectra after the ultraviolet irradiation for respective resins of Example 3 and Comparative Example. As shown in FIG. 4, the resin of Example 3 has higher ultraviolet transmittance than that of the conventional material, and has high transmittance performance from the ultraviolet region to the visible region, then it is found that it is enough for usage of the fluorescence microscope objective lens for a biological system.

Regarding the polymerization initiator contained in the resin precursor composite according to the present application, its type and additive amount can appropriately be chosen. As preferable polymerization initiators for the precursor composite, there are, for example, photo polymerization initiators such as benzophenone, methanesulfonic acid hydroxy benzophenone, benzoic acid o-benzoyl methyl, p-chloro benzophenone, p-dimethylamino benzophenone, benzoin, benzoin allyl ether, benzoin methyl ether, benzoin ethyl ether, benzoin isobutyl ether, benzoin isopropyl ether, acetophenone, diethoxy acetophenone, 1-hydroxy cyclohexyl phenyl ketone, benzyl dimethyl ketal, 2-hydroxy-2-methyl propiophenone, 1-(4-isopropyl phenyl)-2-hydroxy-2-methyl propiophenone, 1-phenyl-1, 2-propane dione-2-o-benzoyl oxime and the like, and thermal polymerization initiators such as azo compound (azobisisobutyronitrile, dimethyl-2,2'-azobisisobutyrate, etc.), and peroxide (benzoyl peroxide, di (t-butyl) peroxide, etc.).

The additive amount can be chosen within a range of 0.05 to 3 wt %, and preferably chosen within a range of 0.07 to 0.7 wt %. Here, the upper limit of the additive amount of the polymerization initiator provides a appropriate range of the ultraviolet transmittance of the resin. In case of exceeding the upper limit above, the ultraviolet transmittance decreases and it would be unavailable for use as a fluorescence microscope objective lens for a biological system. Meanwhile, if the amount of the polymerization initiator is less than the lower limit of the additive amount of the polymerization initiator, in order to cure the resin precursor composite, more irradiation amount is required in case of the photo polymerization initiator, while a longer curing time is required in case of the thermo polymerization initiator. Additionally, there is a possibility that a resin may deteriorate due to light or thermal energy added during the curing, thereby the intensity of autofluorescence may increase.

Figure 5:
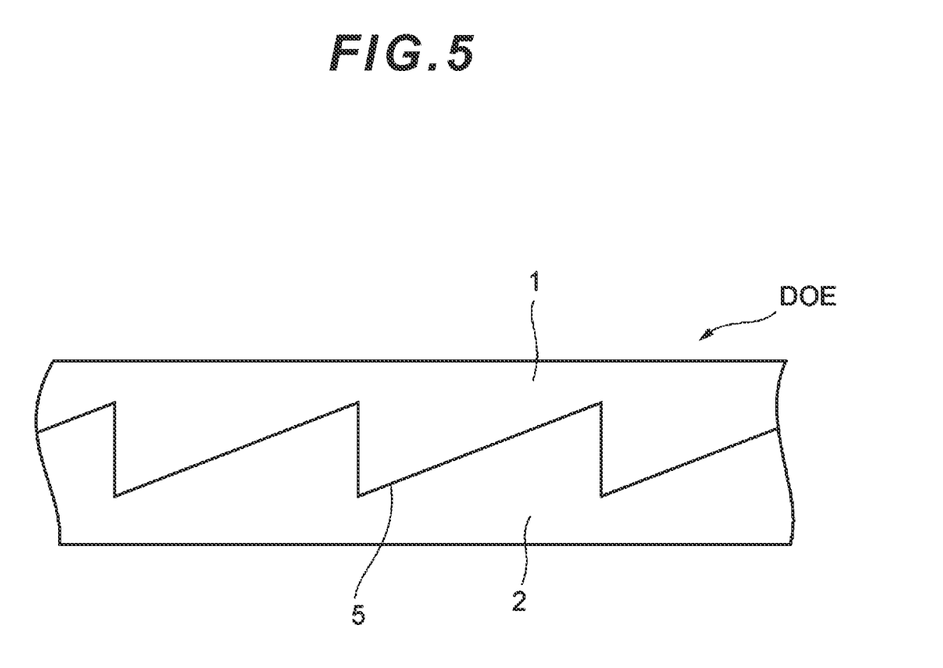
FIG. 5 illustrates a sectional view showing a structure of the bonded-multilayer diffractive optical element composed using the resin having low refractive index and high dispersion according to the present example above.

FIG. 5 shows a structure (cross-sectional configuration) of the bonded-multilayer diffractive optical element. This diffractive optical element comprises a first diffractive optical member 1 composed of a resin having high refractive index and low dispersion, and a second diffractive optical member 2 composed of a resin having low refractive index and high dispersion, and a serrated relief pattern 5 (diffraction grating pattern) formed between the first and the second diffractive optical members 1 and 2. The resin precursor composite reactants of Examples 1, 2, and 3 above are resins having low refractive index and high dispersion, and it is used as a resin of the second diffractive optical member 2.

The resin used for the first diffractive member 1 having high refractive index and low dispersion that is another one of the bonded-multilayer optical members above is explained below.

Any resins, as a resin having high refractive index and low dispersion configuring the first diffractive optical member 1, are available as long as it is a curing reactant of a composite showing high refractive index and low dispersion property. For example, a resin, in which the resin precursor composite is cured using an addition reactant of a composite containing a (meth) acrylate which has a molecular structure having a low dispersibility property and a thiol which has the high refractive index property shown in the following Chemical Expression 2, is preferable.

Chemical Expression 2:

(Chemi. 5)

where, m+n=1 to 6.

The thiol of Chemical Expression 2 is "tricyclodecanedimethanethiol," commonly named "TDDT."

Additionally, as the (meth) acrylate, any kinds of structures are available as long as the (meth) acrylate resin has low dispersibility. For example, as structures having the low dispersibility, there are a norbornene frameworke, a cyclohexane framework, an adamantane framework, and a tricyclodecane framework, etc. The (meth) acrylate having these frameworks are available. Among them, a (meth) acrylate having a tricyclodecane framework shown in Chemical Expression 3 is especially preferable.

Chemical Expression 3:

(Chemi. 6)

where, R=H or $CH_3$, and m+n=1 to 10.

An official name of the acrylate of Chemical Expression 3 is "tricyclodecanedimethanoldi(meth)acrylate," commonly named "TCDA."

Regarding the thiol shown in Chemical Expression 2, since it has higher refractive index and lower dispersion as values of m and n are smaller, the smaller values of m and n are preferable. Accordingly, it is most preferable that m=1 and n=1. In case of the acrylate shown in Chemical Expression 3, it has higher refractive index and lower dispersion according as the values of m and n are smaller.

Accordingly, in the present example, m=1 and n=1 were used in the thiol shown in Chemical Expression 2, m=1, n=1 and R=H were used in the (meth) acrylate shown in Chemical Expression 3.

Additionally, it is appreciated to blend a (meth) acrylate, which has a molecular structure having the low dispersibility property, with a thiol compound having a large rate of Sulfur atoms in the compound, in addition to or instead of a thiol shown in Chemical Expression 2 above. Examples of the compound with a large rate of Sulfur atoms in the compound are 2,5-dimercaptomethyl-1, 4-dithiane (commonly named "DMMD"), cyclohexane-1, 4-diyldimethanethiol, cyclohexane-1, 4-dithiol, bicyclo[2,2,1] heptane-2, 5-dithiol, 5-(1-mercaptoethyl) bicyclo[2,2,2,1] heptane-2-thiol, (2, 5-dimethyl-1, 4-dithian-2, 5-diyl) dimethanethiol, 9-thiabicyclo[3,3,1] nonane-2, 6-dithiol, adamantane-1, 3-dithiol and the like and mixtures of these compounds.

Next, a concrete method for manufacturing this bonded-multilayer diffractive optical element of the present invention, and their properties are described in Examples 4 and 5.

EXAMPLE 4

Figure 6:
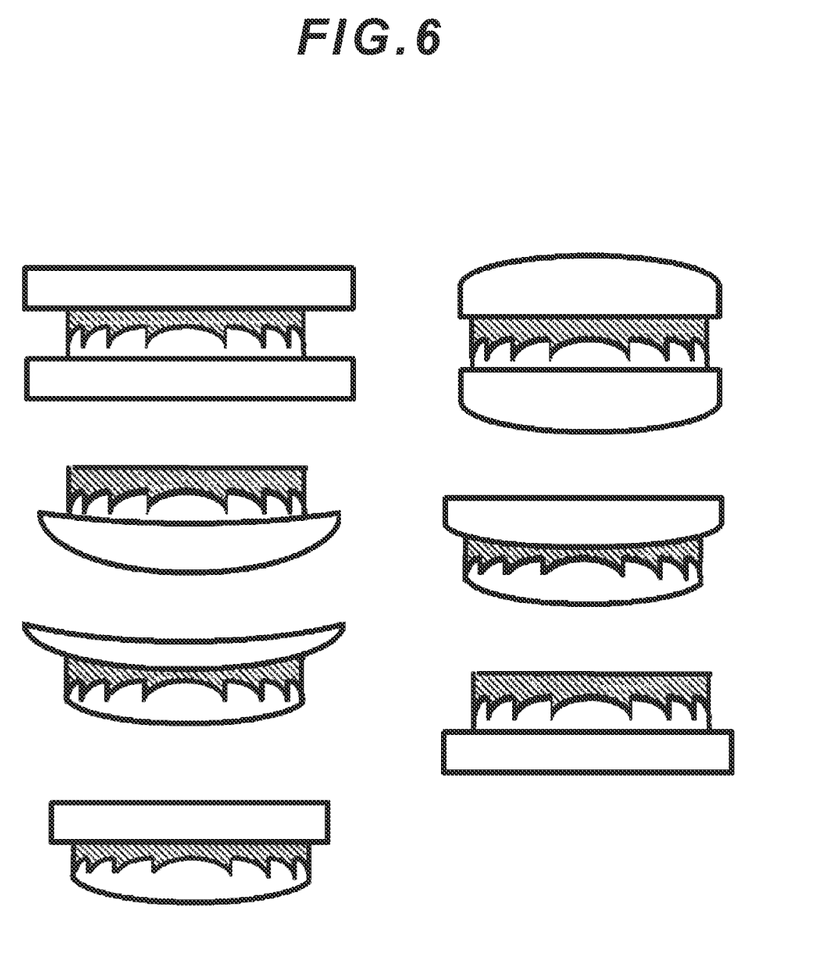
FIG. 6 illustrates a sectional view of a lens having the bonded-multilayer diffractive optical element composed using the resin having low refractive index and high dispersion according to the present example.

According to the present example, in the diffractive optical element shown in FIG. 6, as the first diffractive optical member 1, a cured product of the resin precursor composite obtained through addition reaction in the composition ratio (mole ratio) of 2.5:1 of the TCDA and TDDT above which are the resins having high refractive index and low dispersion mentioned above, was used, while as the second diffractive optical member 2, the 2,2-bis(4-(2-acryloyloxy)ethoxy) phenyl-1,1,1,3,3,3-hexafluoropropane (BAHF) (R=H, m=1, n=1 in Chemical Expression 1 above), and the 2,2-bis(4-(2-(meth)cryloyloxy) ethoxy) phenyl-1,1,1,3,3,3-hexafluoropropane (BMHF) (R=$CH_3$, m=1, n=1 in Chemical Expression 1 above) were used.

Firstly, as low refractive index and high dispersion resin, the resin precursor composite was produced by adding 0.1 wt % of IRGACURE184 (manufactured by BASF Japan, Co. Ltd.), which is the photo polymerization initiator, to the 2,2-bis(4-(2-acryloyloxy)ethoxy) phenyl-1,1,1,3,3,3-hexafluoropropane (BAHF). After injecting this to a certain metal mold of the diffractive optical element, it is pressed by a substrate and irradiated with ultraviolet. The ultraviolet irradiation was performed using the ultraviolet irradiation equipment (manufactured by U-VIX Corporation) having an LED which generates 365 nm ultraviolet. In this situation, through a ground glass, irradiation for 60 seconds was performed at 25 mW/cm² as a provisional curing.

The light source including 365 nm, such as a metal halide lamp, a high-pressure mercury lamp, or an LED, etc., is available. Since the LED was preferable among these in order especially to suppress autofluorescence, the LED was used in the present example. After the provisional curing, the diffractive optical member 2 is completed by being removed from the metal mold.

Next, the resin precursor composite was produced by adding 0.1 wt % of IRGACURE184 (manufactured by BASF Japan Co. Ltd.), which is a photo polymerization initiator, to a Michael addition reactant of a composite (mole ratio TCDA:TDDT=2.5:1) of the thiol (m=n=1) shown in Chemical Expression 2 above and the acrylate (R=H, m=1, n=1) shown in Chemical Expression 3 above. This is injected on the molded diffractive optical member 2, then ultraviolet is irradiated while a substrate is pressed.

The ultraviolet irradiation was performed using the ultraviolet irradiation equipment (manufactured by U-VIX Corporation) having an LED which generates 365 nm ultraviolet. In this situation, through the ground glass, irradiation for 60 seconds was performed at 25 mW/cm² as a provisional curing, and subsequently irradiation for 250 seconds was performed at 40 mW/cm² as a real curing.

EXAMPLE 5

Also, regarding the 2,2-bis(4-(2-(meth)cryloyloxy) ethoxy) phenyl-1,1,1,3,3,3-hexafluoropropane (BMHF), the diffractive optical member 2 was molded as well as (BAHF) and Example 4. In the present example, as high refractive index and low dispersion optical member, the resin precursor composite, which was the Michael addition reactant of the composite (mole ratio TCDA:TDDT=3:1) of the thiol (m=n=1) shown in Chemical Expression 2 above and the methacrylate (R=$CH_3$, m=1, n=1) shown in Chemical Expression 3 above, is used and the diffractive optical member 1 was molded as well as Example 4.

EXAMPLE 4

(Low refractive index and high dispersion optical member) BAHF, IRGACURE184 0.1 wt %

(High refractive index and low dispersion optical member) The addition reactant of TCDA:TDDT=2.5:1, IRGACURE184 0.1 wt %

EXAMPLE 5

(Low refractive index and high dispersion optical member) BMHF, IRGACURE184 0.1 wt %

(High refractive index and low dispersion optical member) The addition reactant of TCDA:TDDT=3:1, IRGACURE184 0.1 wt %

Regarding Examples 4 and 5, Table 2 shows a grating height of the serrated relief pattern 5 (diffraction grating pattern) formed between the first and second diffractive optical members 1 and 2 in FIG. 6. As shown in Table 2, in Example 4, the height of the serrated relief pattern 5 formed between the first and second diffractive optical members 1 and 2 was able to be set as 25.6 µm, and to be set as 25.5 µm in Example 5.

TABLE 2

|  | Low Refractive Index and High Dispersion | High Refractive Index and Low Dispersion (Mole Ratio) | Grating Height [µm] |
|---|---|---|---|
| Example 4 | BAHF | TCDA:TDDT = 2.5:1 | 25.6 |
| Example 5 | BMHF | TCDA:TDDT = 3:1 | 25.5 |

As mentioned above, the grating height of the relief pattern 5 was able to be suppressed down to a very small value in both examples.

Figure 7:
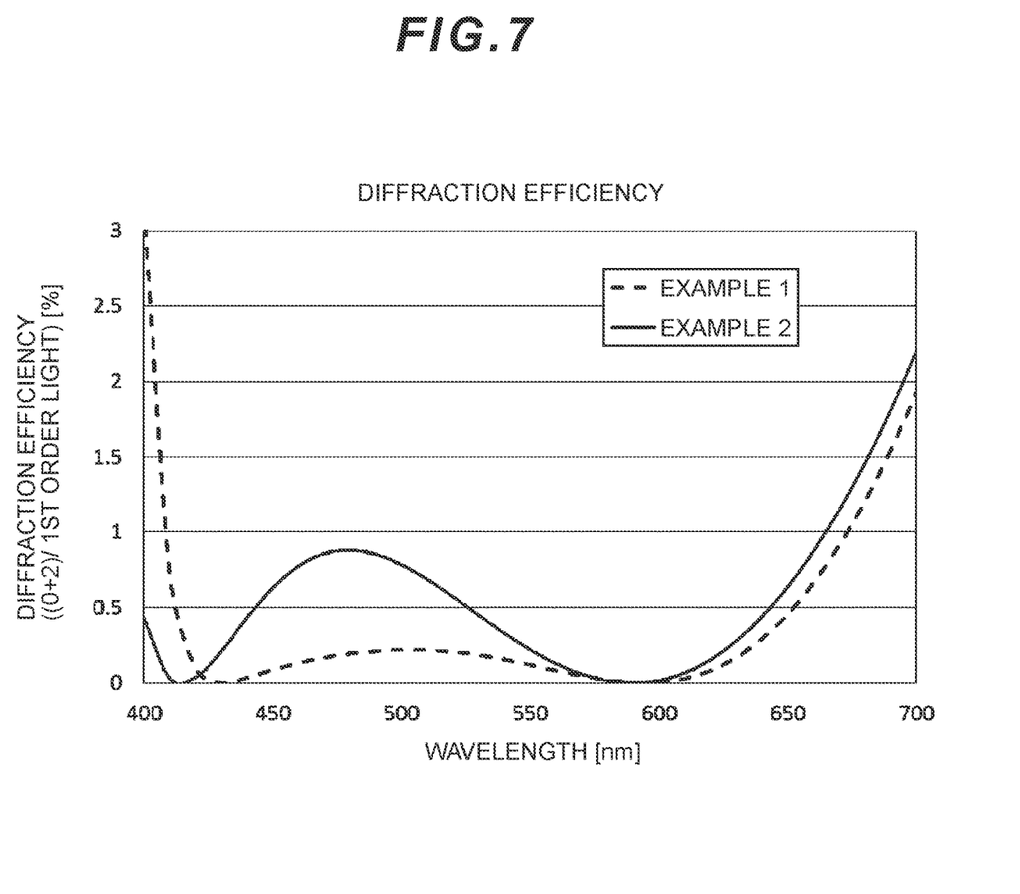
FIG. 7 illustrates a graph showing a diffraction efficiency of the bonded-diffractive optical element composed using the resin having high refractive index and low dispersion and the resin having low refractive index and high dispersion according to the present example.

A diffracted light intensity of an unnecessary diffraction order in the optical lens 10 having this structure is shown in FIG. 7.

The vertical axis is (0+2)/1st order light, and as this value is smaller, it shows that the diffraction performance is more excellent. The diffractive optical element formed in the present examples has a small diffracted light intensity in an unnecessary order, compared with a case using a diffraction optical element formed from the conventional resin, and shows a high diffraction performance. The diffraction efficiency against slant incident lights to the optical axis is also high, and it is available for a wide range of applications, such as a fluorescence microscope objective lens for a biological system, interchangeable lens, binocular, telescope, security camera and projector, etc.

It is, what is called, a bonded-multilayer optical member which is composed of a diffraction grating, in which a resin having high refractive index and low dispersion and a resin having low refractive index and high dispersion are piled, and in which a diffraction grating is formed at a boundary surface. The bonded-multilayer optical member may be formed on one substrate, or may be inserted between two substrates. Any one of high refractive index and low dispersion resin and low refractive index and high dispersion resin can be formed as a first layer.

The substrates may be parallel plates, or may be planoconcave-shaped, planoconvex-shaped, or meniscus-shaped, biconvex-shaped. The bonded-multilayer optical element may be formed on a plane, or may be formed on a convex surface or concave surface. The optical member according to the present invention is widely used for a filming optical system, optical system for a microscope, optical system for observation, etc., and can be configured by adopting a suitable structure appropriately chosen depending on usage or a configuration of the optical systems.

The optical member having low refractive index and high dispersion used in the present invention is not limited to Examples 1 to 5, the resins which is obtained by curing the resin precursor composite containing a bisphenol AF ethyleneoxide modified di (meth) acrylate shown in Chemical Expression 1 above, have the similar properties. The resin precursor may contain a composite which turns into a cured resin by curing, such as any one of a monomer, oligomer, prepolymer, and polymer.

EXPLANATION OF NUMERALS AND CHARACTERS

DOE Diffractive Optical Element
1 First Diffractive Optical Member
2 Second Diffractive Optical Member
5 Relief Pattern (Diffraction Grating Pattern)
10 Lens

The invention claimed is:
1. A diffractive optical element comprising :
 a first optical element obtained by curing a resin precursor composite containing
  a bisphenol AF ethyleneoxide modified di(meth)acrylate which is defined by a Chemical Expression 1-shown below, and
  0. 05 to 3 wt % of a polymerization initiator with respect to an amount of the bisphenol AF ethyleneoxide modified di(meth)acrylate; and
 a second optical element obtained by curing a resin precursor composite containing a thiol which is defined by a Chemical Expression 2-shown below and a di(meth)acrylate; and
 a diffraction grating formed at a boundary surface of the first optical element and the second optical element which are laminated with each other, "Chemical Expression 1":

where, R =H or CH$_3$, and m+n =1 to 10;

"Chemical Expression 2":

where, m+n =1 to 6.

2. The diffractive optical element according to claim 1, wherein in the bisphenol AF ethyleneoxide modified di(meth)acrylate- defined by the Chemical Expression 1, m =1, and n =1.

3. The diffractive optical element according to claim 1, wherein the di(meth)acrylate-is defined by a Chemical Expression 3-shown below,

"Chemical Expression 3":

where, R =H or CH$_3$, and m+n =1 to 10.

4. A diffractive optical element comprising:
a first optical element obtained by curing a resin precursor composite containing
a bisphenol AF ethyleneoxide modified di(meth)acrylate-which is defined by a Chemical Expression 1-shown below, and
0.07 to 0.7 wt % of a polymerization initiator with respect to an amount of the bisphenol AF ethyleneoxide modified di(meth)acrylate; and
a second optical element obtained by curing a resin precursor composite containing a thiol which is defined by a Chemical Expression 2-shown below and a di(meth)acrylate; and
a diffraction grating formed at a boundary surface of the first optical element and the second optical element, which are laminated with each other, "Chemical Expression 1":

where, R =H or CH$_3$, and m+n =1 to 10;

"Chemical Expression 2"

where, m+n =1 to 6.

5. The diffractive optical element according to claim 4, wherein in the bisphenol AF ethyleneoxide modified di(meth)acrylate-defined by the Chemical Expression 1, m =1, and n =1.

6. The diffractive optical element according to claim 4, wherein the-di(meth)acrylate-is defined by a Chemical Expression 3-shown below, "Chemical Expression 3":

where, R =H or CH$_3$, and m+n =1 to 10.

* * * * *